United States Patent [19]

Hedelman

[11] 4,012,144
[45] Mar. 15, 1977

[54] SPECTROSORPTANCE MEASURING SYSTEM AND METHOD

[75] Inventor: Sidney Hedelman, San Francisco, Calif.

[73] Assignee: Varian Associates, Palo Alto, Calif.

[22] Filed: Aug. 7, 1975

[21] Appl. No.: 602,841

[52] U.S. Cl. .............................. 356/73; 356/236; 250/228

[51] Int. Cl.² .................... G01N 21/00; G01J 1/04

[58] Field of Search ............... 356/236, 73, 96, 90, 356/95; 250/228

[56] References Cited

UNITED STATES PATENTS

| 2,707,900 | 5/1955 | Maresh et al. | 356/90 X |
| 3,242,797 | 3/1966 | Sundstrom | 356/95 |
| 3,459,480 | 8/1969 | Prescott et al. | 356/96 |
| 3,746,869 | 7/1973 | Lindstedt et al. | 356/73 |

Primary Examiner—John K. Corbin
Assistant Examiner—Rolf Hille
Attorney, Agent, or Firm—Stanley Z. Cole; Gerald M. Fisher; John J. Morrissey

[57] ABSTRACT

Apparatus and method for measuring the absolute absorptance of a relatively thin sample displaying both reflecting and transmitting characteristics. An integrating sphere is provided, and monochromatic reference and sample beams are projected into the sphere from a pair of angularly-spaced ports. Detector means are positioned at the sphere to receive illumination from the internal sphere wall, including the illumination arising from the first reflectance from that portion of the sphere directly illuminated by the sample and reference beams. The reference and sample electrical signals proceeding from the detector are equalized over the wavelength range of the instrument to establish a relatively flat baseline with the sample withdrawn from the sample beam. The sample is then repositioned within the sample beam. By virtue of the position of the detector and the thinness of the sample, the detector views the illumination of the sphere wall, but substantially excludes the first reflectance and scattered energy from the sample. The light falling on the detector due to illumination of the sphere via the sample is compared with the light falling on the detector due to illumination of the sphere by the reference beam, the ratio between the two providing a direct measure of the quantity of incident sample beam energy transmitted and reflected by said sample. By subtracting the thus determined reflectance and transmittance of the sample from unity, the absorptance of the sample may be directly indicated.

9 Claims, 1 Drawing Figure

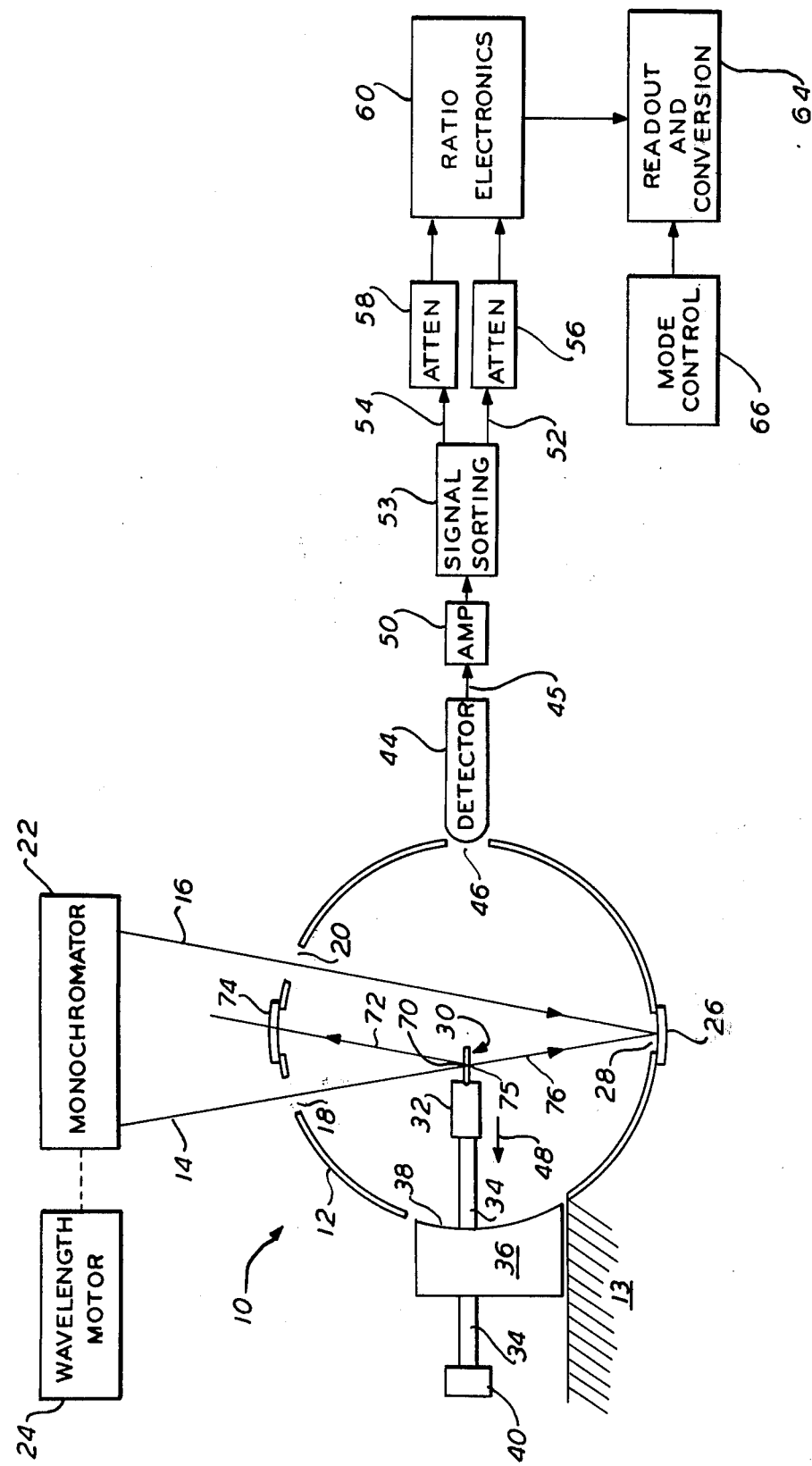

SPECTROSORPTANCE MEASURING SYSTEM AND METHOD

BACKGROUND OF INVENTION

This invention relates generally to apparatus and methods for measuring the absorptance of materials displaying reflecting and transmitting characteristics, and more specifically relates to the measurement of such characteristics by means of an integrating sphere.

In numerous applications of optical technology, it is of interest to establish the absorptance characteristics of samples of material of the type displaying both reflecting and transmitting characteristics. By the term "absorptance" is meant the quantity $[1-(R_s+T_s)]$, where $R_s$ is the reflectance, and $T_s$ is the transmittance of the said sample. The indicated parameter, i.e., absorptance, may, for example, be of interest in connection with evaluation of samples of greenhouse glass, and of glasses and other materials used with solar cells.

To the extent the prior art has been concerned with evaluating optical characteristics of materials of the foregoing type, such art has dealt primarily with the reflectance of such materials. Various instrumentalities have thus been used for such purposes, including integrating spheres — which indeed have long been known for use in evaluating the reflectance characteristics of all types of materials. Reference may usefully be had in this connection, to such articles as D. K. Edwards et al., "Integrating Sphere for Imperfectly Diffuse Samples" 51 *Applied Optics* 1279 (November, 1961); and to David G. Goebel, "Generalized Integrating Sphere Theory;" 6 *Applied Optics* 125 (January, 1967).

While instruments and techniques are also known which are useful in measuring transmittance of samples of the type cited above, in general such prior art (particularly where contemplating the measurement of absolute absorptance) has required two sequential steps of observations. Thus, where use of an integrating sphere has been contemplated, some type of displacement of the integrating sphere, or of the supporting structure between measurements, is commonly prescribed. Further, the integration or summations then performed were commonly enabled through the use of computers, or via other burdensome and costly techniques.

In accordance with the foregoing, it may be regarded as an object of the present invention, to provide apparatus and methods enabling rapid and economical measurement of the absorptance of reflecting and transmitting samples of material.

SUMMARY OF INVENTION

Now in accordance with the present invention, the foregoing object, and others will become apparent in the course of the ensuing specification are achieved by use of an integrating sphere, into which sample and reference beams are projected from a pair of ports displaced to alternate sides of a sphere diameter, so that each beam impinges upon a common diffusely reflecting portion of the sphere interior wall. Detector means, such as a cadium sulfide cell, a photo-multiplier, or so forth, are positioned at the sphere to receive illumination from the internal sphere wall, including illumination arising from the first reflectance of the sphere portion directly illuminated by the sample or reference beams.

With the sample withdrawn from the sample beam, the reference and sample electrical signals proceeding from the detector are compensated over the wavelength range of the instrument, to establish unity ratio between sample and reference signals. The sample is thereafter positioned within the sample beam. By virtue of the position of the detector, and of the thinness of the sample, the detector views the illumination of the sphere wall — but substantially excludes the first reflectance and such optical energy as may be transmitted by the sample, i.e., substantially excludes viewing the specular and scattered components of the reflected and transmitted light until after the light strikes the sphere wall.

The light falling on the detector due to illumination of the sphere via the sample, i.e., the light reflected from and that transmitted through the sample, is compared with the light falling on the detector due to illumination of the sphere by the reference beam. The ratio between these two detected levels provides a direct measure of the quantity of incident sample beam energy transmitted and reflected by the sample — the quantity $(R_s+R_s)$. By subtracting the thus determined reflectance and transmittance of the sample from unity, the absorptance for the sample — as above defined — may be directly indicated.

BRIEF DESCRIPTION OF DRAWINGS

The invention is diagrammatically illustrated by way of example, in the drawing appended hereto, in which:

The FIGURE is a schematic plan view of an integrating sphere, and associated electronic components, forming an absorption measuring system in accordance with the invention.

DESCRIPTION OF PREFERRED EMBODIMENT

In the FIGURE appended hereto, a schematic depiction is set forth of a spectrosorption measuring system 10 in accordance with the present invention. The system 10 is seen to include an integrating sphere 12, which is provided, as is conventional in the present art, with a diffusely reflecting internal coating as, for example, of barium sulfate or of magnesium oxide. Integrating sphere 12 is mounted upon a supporting base generally indicated at 13. A sample beam 14 and a reference beam 16 enter the integrating sphere 12 through a pair of ports 18 and 20, so that the direction of the two beams may be regarded as angularly displaced an approximately equal amount to alternate sides of a diameter of the integrating sphere.

The sample and reference beams are derived from a conventional monochromator 22, which may include a chopper or other equivalent means for splitting the output from a single light source alternately as a function of time into the sample beam 14, and reference beam 16. The monochromator 22, again as is conventional in the present art, includes a wavelength drive mechanism 24 forming part thereof. The wavelength drive mechanism 24, as is also known in the art, includes those elements which enable rotation of a prism, diffraction grating, or other element the angular position of which varies the dispersion of incident light so as to enable production of the relatively discrete wavelengths of interest. Accordingly at any given position of the wavelength mechanism 24, it will be evident that the sample and reference beams 14 and 16 provide a relatively monochromatic output at a particular wavelength which is of interest for purposes of evaluating the absorptance characteristics of the sample being considered by system 10.

The beams 14 and 16 after passing through the sphere interior are rendered incident upon a sphere cap 26, which covers a port 28 at the lower end of integrating sphere 12.

Sphere cap 26 is removable, in that port 28 can serve certain additional functions where the integrating sphere 12 is utilized in other modes of operation. The interior wall of cup 26 is covered with a diffusely reflecting material, such as the barium sulfate or magnesium oxide coatings previously mentioned, and having the same average reflectance as the sphere wall.

The sample 30 which is to be evaluated by means of system 10 is positioned by a sample holder 32, which, in turn, is secured to a shaft 34. The latter passes through a bearing block 36, which block also serves as a cover for port 38. A shaft control means 40, which can be a simple manual or motor-operated device, enables rotation of shaft 34, and also enables axial-wise movement of the shaft 34 through bearing block 36, as to enable partial withdrawal of the sample 30, away from the central portions of sphere 12.

A detector means 44 is mounted at one side of sphere 12, in opposition to the sample 30. The detector 44 specifically is present at a further port 46 at the sphere wall 12. Detector 44 may comprise one of numerous devices well-known for these purposes in the art as, for example, a cadmium sulfide cell, a photo multiplier system, or various solid state devices such as avalanche photodiodes or photo transistors in suitable circuits, etc. The detector 44 may further, include a mask or other aperture limiting device — depending upon the size of the opening represented by port 46 and the specific type of photoreceptor utilized. The net effect of such arrangement is that detector 44 will receive illumination from the internal sphere wall, including specifically illumination arising from the first reflectance of the sample (or reference) beam as such beam is diffusely reflected by the interior wall of cap 26.

During use of system 10, shaft control means 40 is operated so as to withdraw shaft 34 to the left in the sense of the figure, i.e., in the direction of arrow 48, which in turn withdraws the sample 30 from the path of sample beam 14. The sample holder 32, together with sample 30, is not, however, withdrawn completely from the integrating sphere 12 (but rather only toward one side thereof) as it is desired that during the establishment of a baseline, the sample and sample holder be present to perform (by virtue of their various incidental surfaces) an absorbing function comparable to that which such surfaces will perform during subsequent measurement. With the sample thus partially withdrawn, a baseline is established by the usual techniques that are well-known in the art of dual beam spectrophotometry. In particular, as is known in that art, some differences usually exist between the sample and reference electrical signal channels due to unavoidable optical or electrical differences in the beam paths or signal processing circuits. It is, accordingly, necessary to amplify or attenuate the signal in one channel with respect to the other, in order to achieve balance.

Referring specifically to the present FIG., it is seen that the electrical output from detector 44 may be provided via line 45 to an amplifier 50, and thence to a signal sorting means 53, the function of which is to divert those portions of the signal from amplifier 50 which relate to sample beam 14 into a sample signal processing channel 52, and those which derive from reference beam 16 into reference signal processing channel 54. A pair of attenuator means 56 and 58 may be present in the channels 52 and 54, or one such attenuator may be present in one of the said channels. As is well-known in the present art, the one or more attenuator means mentioned may basically comprise a manually activated potentiometer which is coupled to the wavelength adjustment mechanism 24 of monochromator 22. Such a potentiometer has taps at various wavelengths and these are connected to other manually adjusted potentiometers. By careful adjustment of the potentiometers, sometimes called "multipots," it is possible to achieve a nearly flat baseline throughout the entire range of monochromator 22; i.e., the electrical signals in channels 52 and 54 are balanced for substantially the entire wavelength range of monochromator 22.

It may further be noted, that automatic devices can be utilized to effect automatic adjustment of attenuator means 56 and/or 58, such as, for example, an automatic baseline compensator arrangement which is set forth in U.S. Pat. No. 3,986,776 to Kenyon P. George, issued on Sept. 29, 1975, Ser. No. 617,926, and entitled "Automatic Baseline Compensator for Optical Absorbtion Spectroscopy," which patent is assigned to the assignee of the present application. Since the specific baseline compensation scheme utilized in the present invention is not critical to the operation thereof, no further details are deemed required or necessary for an understanding of the present functions.

The electrical signals thus proceeding through channels 52 and 54 thence are provided to a ratio electronics block 60, which provides a direct ratio between the two signals. Where, as mentioned, the signals are balanced, the said ratio will be unity. The ratio signal is then provided via line 62 to a readout and conversion block 64. The latter may include a recorder whereat the baseline can initially be observed and established, i.e., prior to a sample being inserted into sample path 14. During the baseline calibration run a signal from a mode control means 66, assures that a direct ratio of the signals channels 52 and 54 is being read out, in order to enable the baseline calibration operation.

Having established the baseline for the present device, the control means 40 is actuated so as to move sample 30 into the path of sample beam 14. It will be evident that under these conditions, and assuming, as indicated, that the sample 30 is both specularly reflecting and transmitting, the sample beam upon striking the sample 30 at point 70, will be split into two components. The first of these is a specularly reflected component 72, which proceeds toward and impinges on a sphere cap 74, the interior wall of which is provided with the same diffusely reflecting material previously discussed. (It may be noted that the cap 74 is also removable in the event it is desired to remove the reflected beam 72 from further interaction with integrating sphere 12.)

At the same time a second portion 76 of sample beam 14 proceeds via transmission through the sample — as indicated at 75. The transmitted beam 76 thus proceeds in the original direction of beam 14, and thus impinges upon the diffusely reflecting interior of cap 26. It will thus be evident that the overall effect of interposing sample 30, is that the interior sphere wall will in fact be illuminated by an amount of light proportional to the sum of the light intensity reflected and transmitted by sample 30. The sample 30 is assumed to be relatively thin, having, e.g., a typical thickness of the order of 5 mms, and it will be evident from consideration of the arrangement indicated, that detector 44 while viewing, as already indicated, the illumination of the sphere wall, substantially excludes from its view the first reflectance. Under such conditions the ratio between the light falling on the detector due to illuminations via the sample, and that falling on the detector due to illumination by reference beam 16, is equal to the factor $(R_s+T_s)$. This is accordingly to say, that the output from ratio electronics block 60 under these conditions, is precisely the factor $(R_s+T_s)$. During the absorptance readout operation, the mode control block 66 provides a signal to readout and conversion block 64, which assures that the readout represents the difference between unity and the quantity $(R_s+T_s)$, or, in other words, the absorptance as previously defined herein.

If in addition to specularly reflected and transmitted light, diffusely reflected and transmitted light via the sample, illuminates the sphere, then $(R_s+T_s)$ will also be correctly measured in the above system.

While the present invention has been particularly set forth in terms of specific embodiments thereof, it will be understood in view of the present disclosure, that numerous variations upon the invention are now enabled to those skilled in the art, which variations yet reside within the scope of the instant teaching. Accordingly the invention is to be broadly construed, and limited only by the scope and spirit of the claims now appended hereto.

I claim:

1. Apparatus for measuring the absolute absorptance of a relatively thin sample displaying both specularly reflecting and transmitting characteristics, comprising:
   an integrating sphere;
   means for directing relatively monochromatic reference and sample beams into said sphere from a pair of angularly spaced ports;
   detector means positioned at said sphere to receive illumination from said internal sphere wall, including the illumination arising from the first reflectance from that portion of the sphere wall directly illuminated by said sample and reference beams;
   baseline compensator means for equalizing the reference and sample electrical signals from said detector with said sample removed from said sample beam;
   means for positioning said sample within said sphere in the path of said sample beam, and at such position with respect to said detector that said detector views the illumination of the sphere wall, and substantially excludes the specular and scattered components of the reflected and transmitted light energy from said sample until after said energy strikes the sphere wall;
   ratio electronics means for comparing the light falling on said detector due to illumination of the sphere wall via the sample to the light falling on said detector due to illumination by said reference beam, thereby to directly measure the quantity of incident sample beam energy transmitted and reflected by said sample; and
   means for converting the determined ratio into absorptance of the said sample.

2. Apparatus in accordance with claim 1, including monochromator means for generating said reference and sample beams, and means for varying the wavelength of said monochromator output to provide a series of relatively discrete wavelengths for said reference and sample beams.

3. Apparatus in accordance with claim 1, wherein said reference and sample beams are incident from ports displaced approximately equal angular distances from a diameter of said sphere, whereby said beams are incident on a common point of said internal sphere wall.

4. Apparatus in accordance with claim 1, including sample holder means for holding said sample, a bearing block closing a port at one side of said sphere, a shaft extending from said sample holder through said bearing block, and actuator means for displacing said shaft in an inward and outward direction with respect to said sphere, whereby to enable movement of said samples into and out of said sample beam.

5. Apparatus in accordance with claim 1, including a removeable sphere cap mounted at a port of said sphere, at the said common point of incidence of said sample and reference beams, said sphere cap being provided with a diffusely reflecting coating at its side facing internal of said sphere.

6. Apparatus in accordance with claim 5, further including a second sphere cap provided with a diffusely reflecting coating at its internally facing side, said second cap being positioned to intercept the specular reflection from said sample, upon said sample being interposed in said sample beam.

7. A method for measuring the absolute absorptance of a relatively thin sample displaying both reflecting and transmitting characteristics, comprising:
   directing relatively monochromatic reference and sample beams into an integrating sphere from a pair of angularly spaced ports;
   positioning detector means at said sphere to receive illumination from said internal sphere wall, including the illumination arising from the first reflectance from that portion of the sphere wall directly illuminated by said sample beam;
   equalizing the reference and sample electrical signals from said detector means with said sample removed from said sample beam;
   positioning said sample within said sphere in the path of said sample beam, and at such location with respect to said detector means that said means views the illumination of the sphere wall, and substantially excludes the specular and scattered components of the reflected and transmitted light energy from said sample until after said energy stikes the sphere wall;
   forming a ratio between the light intensity falling on said detector due to illumination of the sphere wall via the sample, and the light intensity falling on said detector due to illumination by said reference beam, thereby to directly measure the quantity of incident sample energy transmitted and reflected by said sample; and
   converting the determined ratio into the absorptance of the said sample by deducting said ratio from unity.

8. A method in accordance with claim 7, including varying the wavelengths of said reference and sample beams monochromator output to provide a series of relatively discrete wavelengths for said beams.

9. A method in accordance with claim 7, wherein said reference and sample beams are rendered incident from ports displaced approximately equal angular distances from a diameter of said sphere, whereby said beams are incident on a common point of said internal sphere wall.

* * * * *